(12) United States Patent
Guillou et al.

(10) Patent No.: US 6,565,863 B1
(45) Date of Patent: May 20, 2003

(54) COSMETIC COMPOSITIONS, IN PARTICULAR FOR CLEANSING THE SKIN

(75) Inventors: Veronique Guillou, Antony (FR); Laurence Sebillotte-Arnaud, L'Hay les Roses (FR)

(73) Assignee: L'Oreal, Paris (FR)

( * ) Notice: Subject to any disclaimer, the term of this patent is extended or adjusted under 35 U.S.C. 154(b) by 0 days.

(21) Appl. No.: 09/648,765

(22) Filed: Aug. 28, 2000

(30) Foreign Application Priority Data

Sep. 15, 1999 (FR) .............................. 99 11521

(51) Int. Cl.$^7$ .............................. A61K 7/00; A61K 7/08; C07K 17/00
(52) U.S. Cl. ..................... 424/401; 424/70.19; 530/370
(58) Field of Search .............................. 424/401, 70.19; 530/370

(56) References Cited

U.S. PATENT DOCUMENTS 2,972,582 A 2/1961 Powers et al.
4,540,507 A * 9/1985 Grollier .................. 424/70.19
5,071,960 A 12/1991 Turowski et al.

OTHER PUBLICATIONS

Allison W. C. et al., "Ammonium Cocoyl Isethionate: A New, Mild, High–Foaming Surfactant for Personal Care, HAPPI Household & Personal Products, " vol. 32, No. 5, May 1, 1995, pp. 92, 94, 96, 98, XP000498911.

Ariotto A. et al.: "Skin and Hair Benefit From Wheat Protein," Manufacturing Chemist, vol. 67, No. 2, Feb. 1, 1996, pp. 23–25, XP000682299.

* cited by examiner

Primary Examiner—Sreeni Padmanabhan
Assistant Examiner—Michael A Willis
(74) Attorney, Agent, or Firm—Oblon, Spivak, McClelland, Maier & Neustadt, P.C.

(57) ABSTRACT

A transparent aqueous composition comprising, in a physiologically acceptable medium, (i) at least one acylisethionate, and (ii) at least one protein hydrolysate containing a hydrophobic group, in an amount which is sufficient to dissolve the acylisethionate in the composition.

20 Claims, No Drawings

COSMETIC COMPOSITIONS, IN PARTICULAR FOR CLEANSING THE SKIN

BACKGROUND OF THE INVENTION

1. Field of the Invention

The present invention relates to transparent aqueous compositions containing acylisethionate and protein hydrolysate, and to the use of the said compositions, in particular in cosmetics for cleansing the skin, the hair, the lips and/or the eyes, as well as to the use of a protein hydrolysate for stabilizing an acylisethionate in an aqueous composition.

2. Background of the Invention

Cleansing the skin is very important for facial care. Compositions suited for this purpose should be of the highest possible performance quality, since greasy residues such as the excess of sebum, the residues of the cosmetic products used daily and make-up products, in particular waterproof make-up products, accumulate in the folds of the skin and on the surface of the skin and can block the skin pores and lead to the appearance of spots. Poor-quality cleansing is often among the factors responsible for a muddy complexion.

Among the skin-cleansing products commonly used are foam-forming cleansing products, which generally contain anionic surfactants. Attempts are made in particular to And prepare transparent foam-forming cleansing products since, just like water, transparency is a symbol of purity, and thus of cleanliness. Anionic surfactants which may be used in particular are acylisethionates such as cocoylisethionate, which are particularly advantageous since they produce a dense, fine, voluminous foam. However, these acylisethionates have the drawback of being unstable in aqueous solution: they recrystallize over time, and do so all the more quickly when the temperature is low (i.e., less than or equal to room temperature). On account of this instability, gels containing isethionates cannot be transparent. Consequently, it is impossible to formulate stable transparent foam-forming cleansing products containing an acylisethionate.

According to WO 98/26758, this drawback is overcome by adding an amphoteric surfactant such as an imidazoline derivative or a betaine. However, in order to make the isethionate fully soluble, a high level of amphoteric surfactant is necessary, and thus the amphoteric agent/isethionate weight ratio must be greater than 1. The introduction of an amphoteric agent to such a level as proposed by WO 98/126758 reduces the advantageous performance qualities of the cocoylisethionate, namely the density and creaminess of the foam.

U.S. Pat. No. 2,972,582 discloses a combination of acylisethionate and acyl polypeptide. However, this patent does not teach that acyl polypeptides make it possible to dissolve the acylisethionate and, moreover, describes opaque compositions in which the polypeptide is in insufficient amount to dissolve the acylisethionate, and compositions containing (lanolin) oil which have the drawback of leaving an oily deposit on the skin, which it is desired to avoid by using an oil-free aqueous composition.

Accordingly, there remains a need for a transparent aqueous composition containing an acylisethionate, which is stable over time and which does not have the drawbacks of the compositions described above.

SUMMARY OF THE INVENTION

The Inventors have found, surprisingly, that the recrystallization of acylisethionates can be avoided by means of using protein hydrolysates containing a hydrophobic group. In addition, these compounds allow the foam to retain the qualities obtained with cocoylisethionate, i.e., fineness, density and creaminess of the foam.

Accordingly, the present invention provides a transparent aqueous composition comprising, in a physiologically acceptable medium, (i) at least one acylisethionate, and (ii) at least one protein hydrolysate containing a hydrophobic group, in an amount which is sufficient to dissolve the acylisethionate.

The present invention provides a method of removing make-up from and/or for cleansing the skin, the hair, the lips and/or the eyes, comprising applying the composition of the present invention to the skin, the hair, the lips and/or the eyes.

A more complete appreciation of the invention and many of the attendant advantages thereof will be readily obtained as the same becomes better understood by reference to the following detailed description.

DETAILED DESCRIPTION OF THE INVENTION

The expression "aqueous composition" as used herein refers to an oil-free composition containing water.

The expression "transparent" that when a sheet of newspaper is placed behind a transparent bottle containing the composition, the letters printed on the page can be distinguished.

The expression "physiologically acceptable medium" as used herein refers to a medium which is compatible with the skin, the lips, the scalp, the eyelashes, the eyes and/or the hair.

Moreover, the expression "protein hydrolysate containing a hydrophobic group" refers to a hydrolysis derivative of a protein comprising a hydrophobic group, where the hydrophobic group is naturally present in the protein or is added by reacting the protein and/or the protein hydrolysate with a hydrophobic compound.

The presence of the protein hydrolysate containing a hydrophobic group prevents the recrystallization of the acylisethionate. In addition, the mixture of acylisethionate and protein hydrolysate gives a much more advantageous foam quality than the mixture of acylisethionate and amphoteric agent present in known composition, i.e., a finer and denser foam. Furthermore, the product obtained is easier to rinse off and does not leave a film, unlike known products.

The total amount of protein hydrolysate containing a hydrophobic group in the composition of the invention should be sufficient to dissolve the acylisethionate. In practice, it is at least equal to and preferably greater than the amount by weight of acylisethionate. It preferably ranges from 0.5% to 30% by weight of active material, and more preferably from 1% to 10% by weight of active material, relative to the total weight of the composition. These ranges include all specific values and subranges therebetween, such as 2, 5, 8, 15, 20 and 25% by weight of active material.

Another aspect of the present invention is the use of an effective amount of at least one protein hydrolysate containing a hydrophobic group, to stabilize an acylisethionate in an aqueous composition.

An acylisethionate which may be used in the composition of the invention is a compound of formula (I):

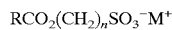

$$RCO_2(CH_2)_nSO_3^-M^+ \quad\quad (I)$$

where
- R is a hydrocarbon-based radical containing from 6 to 26 carbon atoms,
- n is an integer from 2 to 4, and
- M is an ammonium group and/or an alkali metal or alkaline-earth metal, such as sodium, potassium, lithium or magnesium.

According to one preferred embodiment of the invention, the radical R in formula (I) contains from 8 to 22 carbon atoms and is selected from lauroyl, palmitoyl, caproyl, capryloyl, myristoyl, stearoyl, arachidoyl and oleyl radicals and mixtures of such radicals such as the cocoyl radical. M is preferably sodium, potassium and/or an ammonium group.

According to one particularly preferred embodiment of the invention, the acylisethionate used in the composition of the invention is sodium, potassium or ammonium cocoylisethionate.

The acylisethionate is generally present in the composition of the invention in an amount ranging from 0.5 to 15% and preferably from 1 to 10% by weight relative to the total weight of the composition. These ranges include all specific values and subranges therebetween, such as 2, 5, 8 and 12% by weight relative to the total weight of the composition.

As described above, the protein hydrolysate containing a hydrophobic group is a hydrolysis derivative of a protein comprising a hydrophobic group, where the hydrophobic group is naturally present in the protein or maybe added by reacting the protein and/or the protein hydrolysate with a hydrophobic compound. The proteins can be of plant origin or of animal origin, those of plant origin being preferred, and they can be quaternized or non-quaternized, and ionic or nonionic. The hydrophobic group can be, in particular, a fatty chain, for example an alkyl chain containing from 8 to 22 carbon atoms.

As protein hydrolysates containing a hydrophobic group which can be used in the composition according to the invention, examples include protein hydrolysates of plant origin, and in particular those of wheat, soybean, oat or silk proteins, comprising an alkyl chain containing from 8 to 22 carbon atoms, and ionic derivatives of these compounds. The alkyl chain can be in particular a lauryl chain and the ionic derivative can be a sodium, potassium and/or ammonium salt. Specific examples include silk protein hydrolysates modified with lauric acid, and the sodium, potassium and/or ammonium salts thereof, such as the product sold under the name Kawa Silk by Kawaken, wheat protein hydrolysates modified with lauric acid and the sodium, potassium and/or ammonium salts thereof, such as the product sold under the name Aminofoam W OR by Croda and the product sold under the name Proteol LW 30 by SEPPIC, and oat protein hydrolysates modified with lauric acid, and the sodium, potassium and/or ammonium salts thereof, such as the product sold under the name Proteol Oat by SEPPIC.

The cosmetically acceptable aqueous medium of the composition of the invention can consist solely of water or of a mixture of water and a cosmetically acceptable solvent such as a $C_1$–$C_4$ lower alcohol, for instance, ethanol, isopropanol, tert-butanol or n-butanol; polyols such as propylene glycol; glycol ethers.

Water is present in the composition of the invention preferably in an amount ranging from 40 to 95% by weight relative to the total weight of the composition. Advantageously, water represents from 50 to 85% by weight relative to the total weight of the composition. These ranges include all specific values and subranges therein, such as 45, 60, 70, 80 and 90% by weight relative to the total weight of the composition.

The amount of solvent(s) can range, for example, from 1 to 30% by weight and preferably from 2 to 20% by weight relative to the total weight of the composition. These ranges include all specific values and subranges therein, such as 5, 8, 10, 12 and 15% by weight relates to the total weight of the composition.

The term "water" usually means pure water. However, some of the water used in the compositions according to the invention can optionally be chosen from mineral or spring waters. In general, a mineral water is fit for consumption, which is not always the case with a spring water. Each of these waters contains, inter alia, dissolved minerals and trace elements. These waters are known to be used for specific treatment purposes according to the particular trace elements and minerals they contain, such as the moisturization and desensitization of the skin, or the treatment of certain dermatitides. The terms "mineral water" and "spring water" denote not only natural mineral or spring waters, but also natural mineral or spring waters which are enriched with additional mineral and/or trace element constituents, as well as aqueous mineral and/or trace element solutions prepared from purified (demineralized or distilled) water.

A natural spring or mineral water used according to the invention can be chosen, for example, from eau de Vittel, the waters of the Vichy basin, eau d'Uriage, eau de La Roche Posay, eau de La Bourboule, eau d'Enghien-les-Bains, eau de Saint Gervais-les-Bains, eau de Néris-les-Bains, eau d'Allevard-lesBains, eau de Digne, eau de Maiziéres, eau de Neyrac-les-Bains, eau de Lons-le-Saunier, eau des Eaux Bonnes, eau de Rochefort, eau de Saint Christau, eau des Fumades, eau de Tercis-les-Bains, eau d'Uriage-les-Bains and eau d'Avene.

The compositions according to the invention have a final pH generally ranging from 3 to 10. This pH preferably ranges from 5 to 8. These ranges for the pH of the composition include all specific values as subranges therebetween, such as 4, 6, 7 and 9. The pH can be adjusted to the desired value conventionally by adding a base (organic or inorganic) to the composition, for example sodium hydroxide, aqueous ammonia or a primary, secondary or tertiary (poly)amine such as monoethanolamine, diethanolamine, triethanolamine, isopropanolamine or 1,3-propanediamine, or alternatively by adding an organic or inorganic acid such as, for example, citric acid, lactic acid or hydrochloric acid.

According to one preferred embodiment of the invention, the compositions according to the invention may contain a foam-forming surfactant other than the acylisethionate and the protein hydrolysate containing a hydrophobic group. Reference may be made to the publication "Encyclopedia of Chemical Technology, Kirk-Othmer" volume 22, pp. 333–432, 3rd edition, 1979, Wiley, incorporated herein by reference, which describes the main classes of surfactants known to those skilled in the art and their functions, in particular whether or not they are foam-forming.

The foam-forming surfactants can be selected in particular from anionic, amphoteric and nonionic surfactants. Among these classes of surfactant, mention may be made, for example, of:

- as amphoteric surfactants: alkylbetaines such as dimethylbetaine, cocobetaine; alkylsulphobetaines; alkylamidopropylbetaines such as cocoamidopropylbetaine, alkylsultanes such as cocoamidopropylhydroxysultane; alkali metal or alkaline-earth metal alkylcarboxyglycinates; imidazolines; amphoacetates such as disodium cocamphodiacetate;

as anionic surfactants: alkyl phosphates such as sodium lauryl phosphate; alkyl taurates such as sodium methylpalmitoyl taurate; sulphosuccinates such as cocoyl sulphosuccinate, the disodium salt of oxyethylenated lauryl sulphosuccinate; alkyl sulfates such as lauryl triethanolamine sulfate; sarcosinates such as sodium lauryl sarcosinate; alkyl ether sulfates such as sodium lauryl ether sulfate; alkyl ether carboxylates such as oyethylefnated sodium decyl ether carboxylate;

as nonionic surfactants: the compounds of formula (II):

$$R^1O(G)_p \quad (II)$$

where

R$^1$ is a monovalent hydrocarbon-based chain containing from 1 to 30 carbon atoms, G is a sugar derivative containing 5 or 6 carbon atoms, and p is an average statistical value ranging from 1 to 6.

The compounds of formula (II) are described in WO 94/27562, incorporated herein by reference. The alkyl polyglycosides of formula (II) are commercially available as APG®, Glucopon™, or Plantaren™ surfactants from Henkel Corporation, Ambler, Pa., 19002. Examples of such surfactants include but are not limited to:

1. APG® 225-an alkylpolyglycoside in which the alkyl group contains 8 to 10 carbon atoms.
2. APG® 425-an alkyl polyglycoside in which the alkyl group contains 8 to 16 carbon atoms.
3. APG® 625-an alkyl polyglycoside in which the alkyl groups contains 12 to 16 carbon atoms.
4. APG® 300-an alkyl polyglycoside substantially the same as the 325 product above but having a different average degree of polymerization,
5. Glucopon™ 600-an alkylpolyglycoside substantially the same as the 625 product above but having a different average degree of polymerization.
6. Plantaren™ 2000-a C$_{8-16}$ alkyl polyglycoside having an average degree of polymerization of 1.4.
7. Plantare™ 1300-a C$_{12-16}$ alkyl polyglycoside having an average degree of polymerization of 1.6.
8. Plantaren™ 1200-a C$_{12-16}$ alkyl polyglycoside having an average degree of polymerization of 1.4. Other examples include alkyl polyglycoside surfactant compositions which are comprised of mixtures of compounds of formula I wherein G represents a moiety derived from a reducing saccharide containing 5 or 6 carbon atoms; n is a number from 1.8 to 3; and R$^1$ is an alkyl radical having from 8 to 20 carbon atoms. The composition is characterized in that it has increased surfactant properties and an HLB in the range of about 10 to about 16 and a non-Flory distribution of glycosides, which is comprised of a mixture of an alkyl monoglycoside and a mixture of alkyl polyglycosides having varying degrees of polymerization of 2 and higher in progressively decreasing amounts, in which the amount by weight of polyglycoside having a degree of polymerization of 2, or mixtures thereof with the polyglycoside having a degree of polymerization of 3, predominate in relation to the amount of monoglycoside, said composition having an average degree of polymerization of about 1.8 to about 3. Such compositions, also known as peaked alkyl polyglucosides, can be prepared by separation of the monoglycoside from the original reaction mixture of alkyl monoglycoside and alkyl polyglycosides after removal of the alcohol. This separation may be carried out by molecular distillation and normally results in the removal of about 70–95% by weight of the alkyl monoglycosides. After removal of the alkyl monoglycosides, the relative distribution of the various components, mono- and polyglycosides, in the resulting product changes and the concentration in the product of the polyglycosides relative to the monoglycoside increases as well as the concentration of individual polyglycosides to the total, i.e. DP2 and DP3 fractions in relation to the sum of all DP fractions. Such compositions are disclosed in copending application Ser. No. 07/810,588, filed on Dec. 19, 1991, the entire contents of which are incorporated herein by reference. The amount of the alkyl polyglycoside which can be used in the shampoo compositions according to the invention can range from 5 to 20% by weight, preferably from 10% to 15% by weight. The preferred compounds are alkyl polyglycosides such as decylglucoside and laurylglucoside sold under the names Plantaren 2000, Plantaren 1200 and Plantacare 200 UP.

Another foam-forming surfactant preferably used is an alkylpolyglycoside and more particularly decylglucoside or laurylglucoside, or mixtures thereof. The addition of alkylpolyglycoside to the composition of the invention has the advantage of increasing the volume of the foam obtained with the said composition, while at the same time giving a composition which is tolerated very well and which rinses out easily.

According to this embodiment, another aspect of the invention is an aqueous composition comprising, in a physiologically acceptable medium, (i) at least one acylisethionate, (ii) at least one protein hydrolysate containing a hydrophobic group in an amount which is sufficient to dissolve the acylisethionate, and (iii) an alkylpolyglucoside.

The foam-forming surfactants other than acylisethionate and the protein hydrolysate containing a hydrophobic group can be present in an amount ranging from 0.5 to 15% by weight and preferably from 1 to 10% by weight relative to the total weight of the composition. These ranges include all specific values and subranges therein, such as 2, 5, 8 and 12% by weight relative to the total weight of the composition.

The compositions of the invention may also contain water-soluble or liposoluble adjuvants that are common in cosmetics, such as preserving agents, antioxidants, fragrances, dyestuffs, nacres, hydrophilic or lipophilic active agents, viscosity modifiers and thickeners or other agents whose effect is to improve the cosmetic properties of hair or skin, such as anionic, nonionic, cationic or amphoteric polymers. These adjuvants and their concentrations should be such that they do not modify the property desired for the composition.

Active agents which may be mentioned, for example, are moisturizers and in particular polyols such as propylene glycol, 1,3-butylene glycol, glycerol, polyglycerols, sugars and sorbitol; ceramides and pseudoceramides; hydroxy acids; vitamins; antidandruff or antiseborrhoeic agents; sunscreens free-radical scavengers.

Viscosity modifiers which may be mentioned in particular are alkoxylated fatty alcohols and fatty esters such as the products Ceteareth-60 myristyl glycol, PEG-120 methylglucose dioleate and PEG-150 pentaerythrityl tetrastearate (CTFA name).

The composition can in particular constitute a cosmetic composition, which can be used more particularly for cleansing and/or removing make-up from the skin, the hair, the lips and/or the eyes. It can more especially constitute a transparent foam-forming cleansing gel.

A subject of the present invention is also a cosmetic process for removing make-up from and/or for cleansing the skin, the hair, the lips and/or the eyes, characterized in that a composition as defined above is applied to the skin, the hair, the lips and/or the eyes.

A subject of the invention is also the cosmetic use of the composition as defined above for removing make-up from and/or for cleansing the skin, the hair, the lips and/or the eyes.

EXAMPLES

Having generally described this invention, a further understanding can be obtained by reference to certain specific examples which are provided herein for purposes of illustration only and are not intended to be limiting unless otherwise specified. The compounds therein are given in the CTFA name and the amounts therein are given as percentages by weight of active material, except where otherwise mentioned.

| Example: Foam-forming gel | |
|---|---|
| Sodium cocoylisethionate (Jordapon CI P ® from the company Jordan) | 3.25% |
| Decylglucoside (Plantacare 2000 UP ® from the company Henkel) | 3.25% |
| Potassium lauroyl wheat amino acids (Aminofoam W OR ® from the company Croda) | 3.25% |
| PEG-120 methyl glucose dioleate (Glucamate DOE-120 vegetal ® from the company Amerchol) | 4% |
| Sorbitol | 3.5% |
| Glycerol | 3.5% |
| Preserving agents | 0.5% |
| Water qs | 100% |

A transparent fluid gel with a viscosity of about 500 mPa.s, measured using a Rheomat RM 180, spindle 3, at 25° C., is obtained, the foam-forming power of which is satisfactory.

Obviously, numerous modifications and variations of the present invention are possible in light of the above teachings. It is therefore to be understood that within the scope of the appended claims, the invention may be practiced otherwise than as specifically described herein.

This application is based on French Patent Application Serial No. 99-11521, filed on Sep. 15, 1999, and incorporated herein by reference in its entirety.

What is claimed is:

1. A transparent aqueous composition, comprising:
in a physiologically acceptable medium, (i) at least one acylisethionate having formula (I)

wherein
R is a hydrocarbon-based radical containing from 6 to 26 carbon atoms,
n is an integer from 2 to 4, and
M is an alkali metal or alkaline-earth metal, the acylisethionate being present in an amount ranging from 0.5 to 10% by weight relative to the total weight of the composition, and (ii) at least one protein hydrolysate containing a hydrophobic group, in an amount which is sufficient to dissolve the acylisethionate, the amount by weight of active material of protein hydrolyzate containing a hydrophobic group being greater than the amount by weight of acylisethionate.

2. The composition of claim 1, wherein R is a cocoyl radical and M is sodium or potassium.

3. The composition of claim 1, wherein the hydrophobic group of the protein hyryol sate is an alkyl chain containing from 8 to 22 carbon atoms.

4. The composition of claim 1, wherein the hydrophobic group is a lauryl chain.

5. The composition of claim 1, wherein the protein hydrolysate containing a hydrophobic group is selected from the group consisting of silk, soybean, wheat and oat protein hydrolysates.

6. The composition of claim 1, wherein the protein hydrolysate containing a hydrophobic group is selected from the group consisting of silk protein hydrolysates modified with lauric acid, wheat protein hydrolysates modified with lauric acid and oat protein hydrolysates modified with lauric acid, salts thereof, and mixtures thereof.

7. The composition of claim 1, wherein water is present in an amount ranging from 40 to 95% by weight relative to the total weight of the composition.

8. The composition of claim 1, further comprising an additional foam-forming surfactant.

9. The composition of claim 8, wherein the foam-forming surfactant is a nonionic surfactant.

10. The composition of claim 9, wherein the nonionic surfactant is represented by formula (II):

wherein
$R^1$ is a monovalent hydrocarbon-based chain containing from 1 to 30 carbon atoms,
G is a sugar containing 5 or 6 carbon atoms, and
p is an average statistical value ranging from 1 to 6.

11. The composition of claim 9, wherein the nonionic surfactant is chosen from decylglucoside and laurylglucoside, and mixtures thereof.

12. The composition of claim 1, which is a cosmetically suitable composition.

13. The composition of claim 1, which is in the form of a transparent gel.

14. A transparent aqueous composition, comprising:
in a physiologically acceptable medium, (i) at least one acylisethionate having formula (I):

wherein
R is a hydrocarbon-based radical containing from 6 to 26 carbon atoms,
n is an integer from 2 to 4, and
M is an alkali metal or alkaline-earth metal, the acylisethionate being present in an amount ranging from 0.5 to 10% by weight relative to the total weight of the composition, (ii) at least one protein hydrolysate containing a hydrophobic group, in an amount which is sufficient to dissolve the acylisethionate, the amount by weight of active material of protein hydrolyzate containing a hydrophobic group being greater than the amount by weight of acylisethionate, and (iii) an alkylpolyglucoside.

15. The composition of claim 14, which is a cosmetically suitable composition.

16. The composition of claim 14, gwhich is in the form of a transparent gel.

17. A method of removing make-up from and/or for cleansing the skin, the hair, the lips and/or the eyes, comprising applying the composition claim 1 to the skin, the hair, the lips and/or the eyes.

18. A method of removing make-up from and/or for cleansing the skin, the hair, the lips and/or the eyes, comprising applying the composition claim 14 to the skin, the hair, the lips and/or the eyes.

19. A method of preparing the composition of claim 1, comprising combining water, (i) and (ii).

20. A method of preparing the composition of claim 14, comprising combining water, (i), (ii) and (iii).

* * * * *

UNITED STATES PATENT AND TRADEMARK OFFICE
CERTIFICATE OF CORRECTION

PATENT NO.    : 6,565,863 B1
DATED         : May 20, 2003
INVENTOR(S)   : Veronique Guillou et al.

It is certified that error appears in the above-identified patent and that said Letters Patent is hereby corrected as shown below:

Column 8,
Line 2, "hyryol sate" should read -- hydrolysate --.

Column 9,
Line 1, "gwhich" should read -- which --.

Signed and Sealed this

Twenty-second Day of July, 2003

JAMES E. ROGAN
*Director of the United States Patent and Trademark Office*